(12) United States Patent
Suematsu et al.

(10) Patent No.: US 10,355,347 B2
(45) Date of Patent: Jul. 16, 2019

(54) HIGH FREQUENCY DEVICE

(71) Applicant: SHARP KABUSHIKI KAISHA, Sakai, Osaka (JP)

(72) Inventors: Eiji Suematsu, Sakai (JP); Keisuke Satoh, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 2 days.

(21) Appl. No.: 15/744,542

(22) PCT Filed: Jun. 7, 2016

(86) PCT No.: PCT/JP2016/066968
§ 371 (c)(1),
(2) Date: Jan. 12, 2018

(87) PCT Pub. No.: WO2017/033525
PCT Pub. Date: Mar. 2, 2017

(65) Prior Publication Data
US 2019/0006745 A1 Jan. 3, 2019

(30) Foreign Application Priority Data

Aug. 26, 2015 (JP) ................................. 2015-166906

(51) Int. Cl.
*H01Q 1/36* (2006.01)
*H01Q 1/38* (2006.01)
(Continued)

(52) U.S. Cl.
CPC ............. *H01Q 1/36* (2013.01); *A61B 5/0507* (2013.01); *G01S 7/032* (2013.01); *H01P 3/06* (2013.01); *H01Q 9/045* (2013.01); *H01Q 21/065* (2013.01); *H03H 7/0153* (2013.01); *A61B 2562/0228* (2013.01); *G01S 13/50* (2013.01);
(Continued)

(58) Field of Classification Search
CPC ..... H01P 3/06; H01P 3/08; H01P 5/08; H01Q 1/38; H01Q 13/08; H01Q 1/36; H01Q 23/00; H01Q 21/065; H01Q 9/04; H01Q 9/045; H03H 7/0153; A61B 5/0507
See application file for complete search history.

(56) References Cited

U.S. PATENT DOCUMENTS 4,360,813 A * 11/1982 Fitzsimmons ....... H01Q 21/064
342/350
4,987,421 A * 1/1991 Sunahara ......... G06K 19/07786
343/700 MS
(Continued)

FOREIGN PATENT DOCUMENTS

| JP | 06-326510 A | 11/1994 |
|---|---|---|
| JP | 07-066627 A | 3/1995 |
| JP | 2687003 B2 | 12/1997 |

*Primary Examiner* — Tho G Phan
(74) *Attorney, Agent, or Firm* — ScienBiziP, P.C.

(57) ABSTRACT

An area and a size of a high frequency device are reduced. The high frequency device includes a first board (1) that has a first surface (1a) on which a circuit unit is formed and a second surface (1b) on which a ground conductor is formed, a second board (2) that has a third surface (2a) on which an antenna is formed and a fourth surface (2b) on which a second ground conductor is formed, and a conductor plate (3), in which the conductor plate (3) is sandwiched between the second surface (1b) and the fourth surface (2b).

8 Claims, 9 Drawing Sheets

| 1: FIRST BOARD | 13b: DIELECTRIC RESONATOR |
|---|---|
| 1a: FIRST SURFACE | 14: TRANSMISSION AMPLIFIER |
| 1b: SECOND SURFACE | 21a: TRANSMISSION PATCH |
| 2: SECOND BOARD | 22: RECEPTION CONNECTION UNIT |
| 2a: THIRD SURFACE | 22c: THROUGH HOLE |
| 2b: FOURTH SURFACE | 22d: CONDUCTOR PIN |
| 3: CONDUCTOR PLATE | 34: SCREW |
| 4: LINE | 35: THROUGH HOLE FOR SCREW |
| 6: CONDUCTOR PATTERN | 36: SCREW RECEIVER |
| 11a: TRANSMISSION PATCH | 37: ARMOR |
| 12: TRANSMISSION CONNECTION UNIT | 38: FREQUENCY CONTROL SCREW |
| 12c: THROUGH HOLE | 44: VIA HOLE |
| 12d: CONDUCTOR PIN | 45: PARTITION CONDUCTOR |
| 13: OSCILLATOR | 100: HIGH FREQUENCY DEVICE |

(51) Int. Cl.
*A61B 5/05* (2006.01)
*G01S 7/03* (2006.01)
*H01P 3/06* (2006.01)
*H01Q 9/04* (2006.01)
*H03H 7/01* (2006.01)
*H01Q 21/06* (2006.01)
*G01S 13/50* (2006.01)
*G01S 7/02* (2006.01)
*H01Q 1/22* (2006.01)

(52) U.S. Cl.
CPC ...... *G01S 2007/028* (2013.01); *H01Q 1/2283* (2013.01)

(56) References Cited

U.S. PATENT DOCUMENTS

| | | | | |
|---|---|---|---|---|
| 5,801,660 | A * | 9/1998 | Ohtsuka | H01Q 9/0414 343/700 MS |
| 6,184,828 | B1 | 2/2001 | Shoki | |
| 6,392,600 | B1 * | 5/2002 | Carson | H01Q 1/246 343/700 MS |
| 7,283,100 | B2 * | 10/2007 | Thompson | H01Q 1/3275 343/700 MS |
| 7,379,023 | B2 * | 5/2008 | Yamanaka | H01Q 9/0407 343/700 MS |
| 7,812,769 | B2 * | 10/2010 | Mizuno | G06K 7/10346 343/700 MS |

* cited by examiner

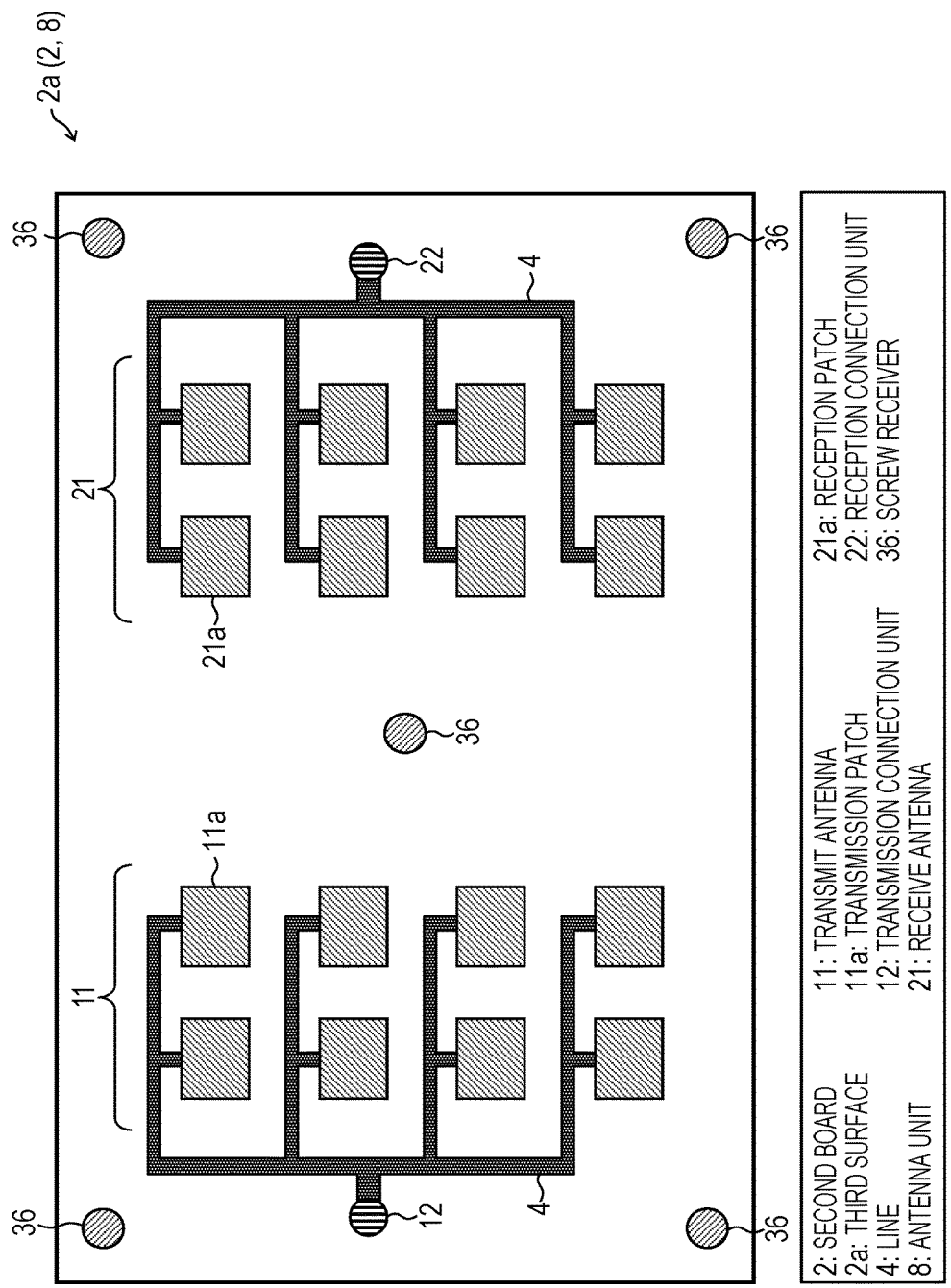

FIG. 4

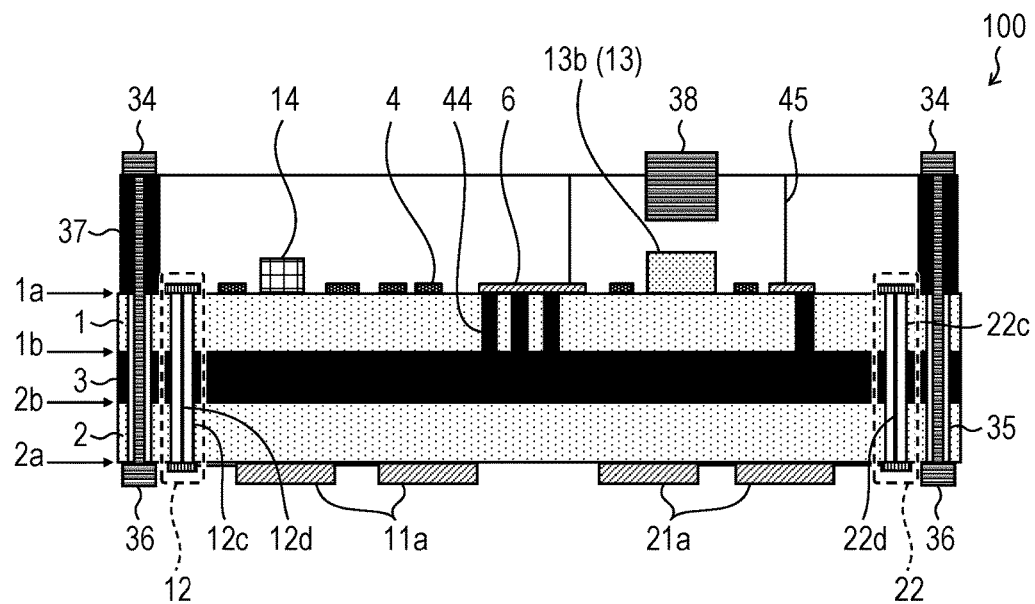

1: FIRST BOARD
1a: FIRST SURFACE
1b: SECOND SURFACE
2: SECOND BOARD
2a: THIRD SURFACE
2b: FOURTH SURFACE
3: CONDUCTOR PLATE
4: LINE
6: CONDUCTOR PATTERN
11a: TRANSMISSION PATCH
12: TRANSMISSION CONNECTION UNIT
12c: THROUGH HOLE
12d: CONDUCTOR PIN
13: OSCILLATOR

13b: DIELECTRIC RESONATOR
14: TRANSMISSION AMPLIFIER
21a: TRANSMISSION PATCH
22: RECEPTION CONNECTION UNIT
22c: THROUGH HOLE
22d: CONDUCTOR PIN
34: SCREW
35: THROUGH HOLE FOR SCREW
36: SCREW RECEIVER
37: ARMOR
38: FREQUENCY CONTROL SCREW
44: VIA HOLE
45: PARTITION CONDUCTOR
100: HIGH FREQUENCY DEVICE

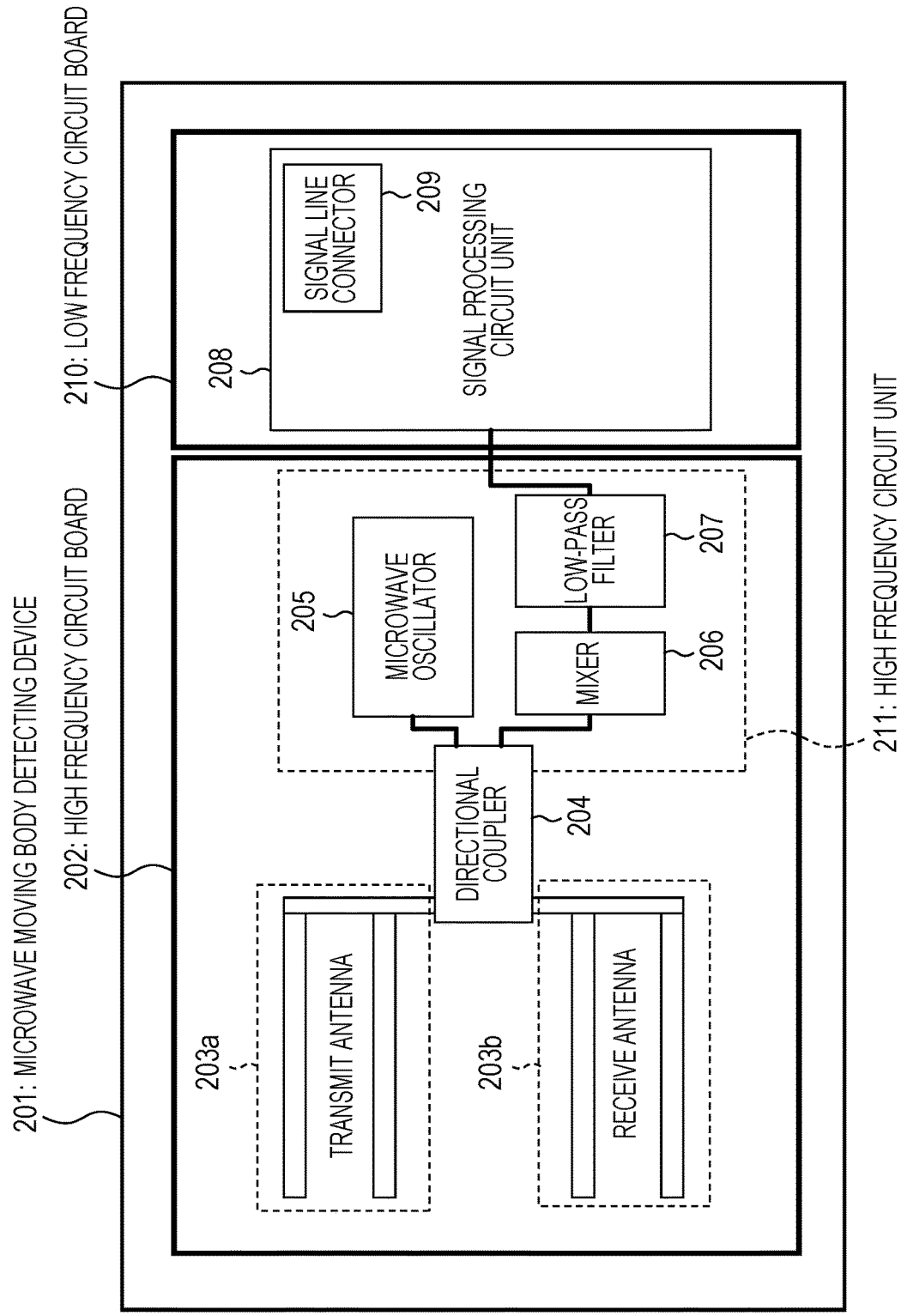

HIGH FREQUENCY DEVICE

TECHNICAL FIELD

The present invention relates to a high frequency device, and particularly relates to a high frequency device that includes an antenna.

BACKGROUND

A high frequency device that includes an antenna is used for various purposes such as radar or communication. For example, PTL 1 discloses a microwave moving body detecting device.

FIG. 9 is a block diagram illustrating a schematic configuration of a microwave moving body detecting device 201 of PTL 1.

The microwave moving body detecting device 201 includes a high frequency circuit board 202 having a transmit antenna 203a, a receive antenna 203b, and a high frequency circuit unit 211 and a low frequency circuit board 210 having a signal processing circuit unit 208, and has an operation frequency of 10 GHz.

A microwave oscillated by a microwave oscillator 205 is emitted into a space from the transmit antenna 203 via a directional coupler 204. The microwave reflected by a moving body in the space is received by the receive antenna 203b. The received microwave passes through the directional coupler 204 and is superposed, in a mixer 206, on the microwave oscillated by the microwave oscillator 205 to be a Doppler signal which is proportional to a speed of the moving body. The Doppler signal passes through a low-pass filter 207 and is input to a signal processing unit 208. The signal processing circuit unit 208 selectively amplifies a frequency component which is generated by movement of a person, detects a motion of the person on the basis of amplitude, a duration time, or the like, and outputs a detection signal from a signal line connector 209.

CITATION LIST

Patent Literature

PTL 1: Japanese Patent No. 2687003 (issued on Dec. 8, 1997)

SUMMARY OF INVENTION

Technical Problem

However, in the microwave moving body detecting device 201 of PTL 1, the receive antenna 203a, the transmit antenna 203b, and the high frequency circuit unit 211 are formed on the same surface of the high frequency circuit board 202. Therefore, it is difficult to reduce an area of the high frequency circuit board 202. Furthermore, the signal processing circuit unit is separately formed on the low frequency circuit board 210, but is formed on the same plane with the receive antenna 203a, the transmit antenna 203b, and the high frequency circuit unit 211. Thus, it is difficult to reduce an area and a size of the microwave moving body detecting device 201.

Solution to Problem

In order to solve the aforementioned problems, a high frequency device according to an aspect of the invention includes: a first single layer board that includes a first surface on which a high frequency circuit is formed and a second surface on which a first ground conductor is formed; a second single layer board that includes a third surface on which an antenna is formed and a fourth surface on which a second ground conductor is formed; and a conductor plate, in which the conductor plate is sandwiched between the second surface and the fourth surface.

Advantageous Effects of Invention

According to the aspect of the invention, the circuit is formed on the first single layer board, and the antenna is formed on the second single layer board. Accordingly, it is possible to select, for the first single layer board, a board which is the most suitable for forming the circuit thereon and select, for the second single layer board, a board which is the most suitable for forming the antenna thereon. Therefore, it is also possible to combine single layer boards that are different in a thickness and a permittivity, thus making it possible to enhance efficiency of each of the circuit and the antenna.

Moreover, according to the aspect of the invention, the first single layer board and the second single layer board sandwich the conductor plate to form a sandwich structure. It is therefore possible to integrally handle the first single layer board, the second single layer board, and the conductor plate as one multi-layer board. In a case where they are handled as one multi-layer board, the first surface and the third surface serve as front and rear surfaces of the substantially one multi-layer board, and the circuit and the antenna are formed on the front and rear surfaces of the substantially one multi-layer board.

Accordingly, it is possible to provide the circuit on a rear surface (opposite surface) of the antenna that requires a large area and arrange the circuit and the antenna efficiently in terms of an area. Thus, it is possible to efficiently reduce an area and a size of the high frequency device.

Moreover, according to the aspect of the invention, the first ground conductor, the second ground conductor, and the conductor plate are electrically integrated and become a ground conductor with respect to the first single layer board and the second single layer board. In addition, the conductor plate is a good ground conductor in a direct current and in a wide frequency band from a low frequency to a high frequency. Therefore, in the high frequency device, ground is difficult to be floated in the wide frequency band.

Since the conductor plate is a good ground conductor, impedances of the circuit and the antenna do not fluctuate and are stabilized. As being stabilized, impedance is easy to be matched in an inside of the circuit, in an inside of the antenna, and between the circuit and the antenna. Moreover, by matching impedance, it is possible to efficiently transmit signal power. It is therefore possible to improve power efficiency of the high frequency device, reduce power consumption and heat generation of the high frequency device, and reduce the size of the high frequency device.

With the aforementioned configuration, the circuit and the antenna share the conductor plate as the around conductor and the impedance is stable, so that designing of the impedance is easy.

BRIEF DESCRIPTION OF DRAWINGS

FIG. 3 is a plan view illustrating a schematic configuration of an antenna unit of the high frequency device illustrated in FIG. 1, and illustrates a third surface of a second board.

FIG. 4 is a cross sectional view illustrating a schematic configuration of the high frequency device illustrated in FIG. 1 and illustrates a cross section taken along an arrow A-B-C-D-E-F-J-H-I-J of FIG. 2.

FIG. 5(a) illustrates a second surface of the first board, FIG. 5(b) illustrates a conductor plate, and FIG. 5(c) illustrates a fourth surface of the second board.

FIG. 9 is a block diagram illustrating a schematic configuration of a microwave moving body detecting device 201 of PTL 1.

DESCRIPTION OF EMBODIMENTS

Embodiment 1

Figure 1:
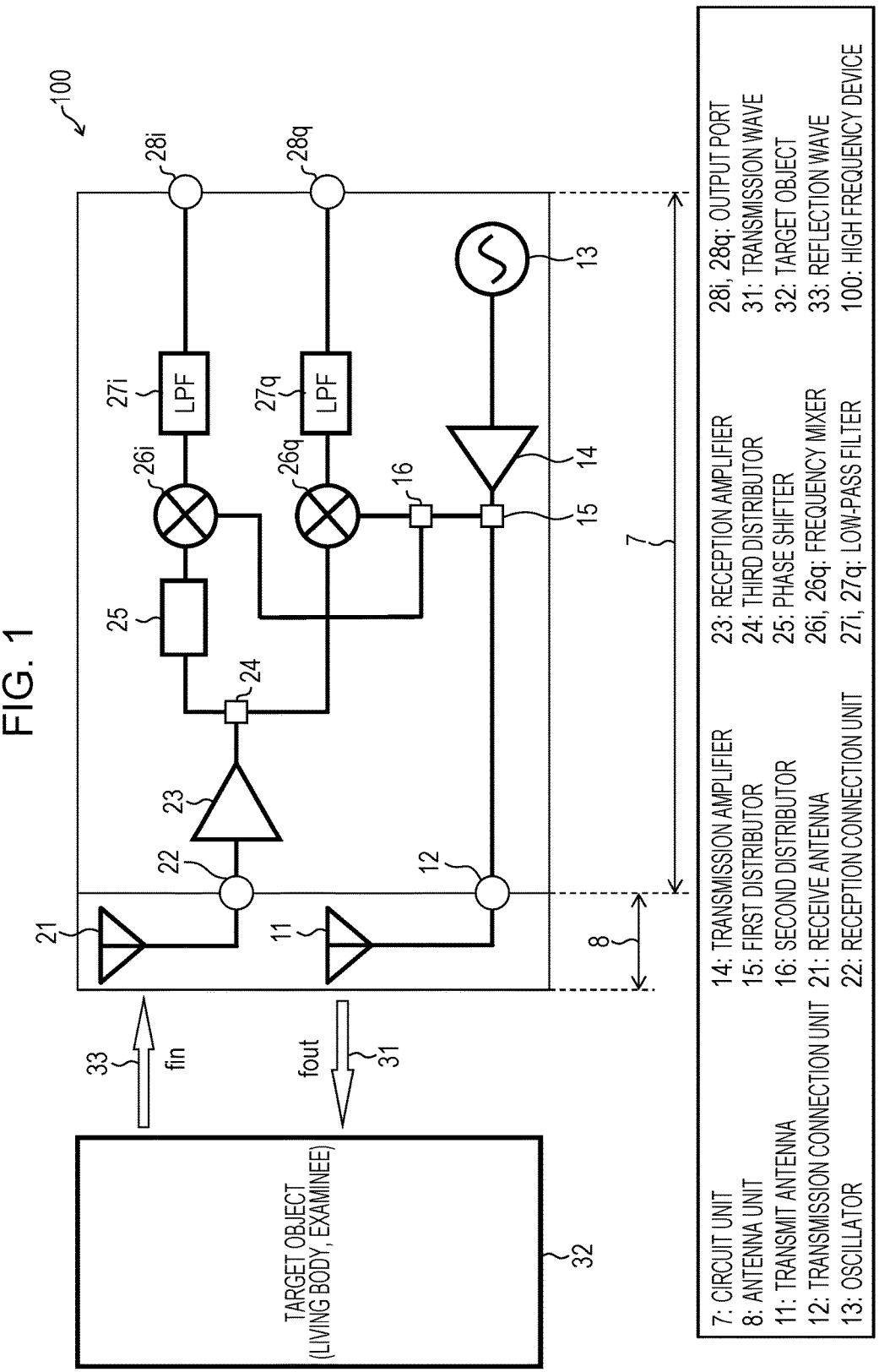
FIG. 1 is a block diagram illustrating a schematic circuit configuration of a high frequency device according to Embodiment 1 of the invention.

Hereinafter, Embodiment 1 of the invention will be described in detail on the basis of FIG. 1 to FIG. 5.
(Circuit Configuration)
FIG. 1 is a block diagram illustrating a schematic circuit configuration of a high frequency device 100 according to Embodiment 1 of the invention. Note that, for simplification of illustration, ground, a power source, and the like are omitted in FIG. 1.

The high frequency device 100 includes a circuit unit (high frequency circuit) 7, an antenna unit (antenna) 8, a transmission connection unit 12, and a reception connection unit 22, and the circuit unit 7 and the antenna unit 8 are connected by the transmission connection unit 12 and the reception connection unit 22.

The circuit unit 7 includes an oscillator 13, a transmission amplifier 14, a first distributor 15, a second distributor 16, a reception amplifier 23, a third distributor 24, a phase shifter 25, frequency mixers 26i and 26q, low-pass filters 27i and 27q, output ports 28i and 28q, a power source circuit (not illustrated), and the like. The circuit unit 7 is a transmission circuit that performs processing for a signal transmitted from the antenna unit 8, a reception circuit that performs processing for a signal received by the antenna unit 8, and a high frequency circuit that operates with a high frequency.

The antenna unit 8 includes a transmit antenna 11 and a receive antenna 21.

The oscillator 13 is an oscillator that oscillates a transmission wave, and oscillates a microwave of 24 GHz. Note that, the oscillator 13 may oscillate a high frequency such as a microwave of a different frequency or a millimeter wave.

The transmission amplifier 14 is a low noise amplifier that amplifies the transmission wave oscillated by the oscillator 13 and a one-stage source grounded microwave field effect transistor. In a case where a ground inductance is sufficiently low, the source grounded field effect transistor exhibits excellent gain characteristics in a wide frequency band.

The first distributor 15 is a distributor that equally distributes the transmission wave, which is amplified by the transmission amplifier 14, into two, and is a Wilkinson distributor. One of the transmission waves distributed by the first distributor 15 reaches the transmit antenna 11 via the transmission connection unit 12, and the other reaches the second distributor 16.

The second distributor 16 is a distributor that equally distributes the other of the transmission waves, which are equally distributed into two by the first distributor 15, into two, and is a Wilkinson distributor. One of carrier waves distributed by the second distributor 16 reaches the frequency mixer 26i, and the other reaches the frequency mixer 26q.

The transmit antenna 11 is connected to the oscillator 13 via the transmission connection unit 12, the transmission amplifier 14, and the first distributor 15, and emits the transmission wave oscillated by the oscillator 13.

A transmission wave 31 is emitted from the transmit antenna 11, and reflected by a target object 32.

The target object 32 is an examinee, but is not limited thereto. The target object 32 may be a living body, an object that reflects the transmission wave 31, or the like.

A reflection wave 33 is the transmission wave 31 that has been reflected by the target object 32, and modulated from the transmission wave 31 due to the Doppler effect in accordance with a motion of the target object 32.

The receive antenna 21 receives the reflection wave 33.

The reception amplifier 23 is connected to the receive antenna 21 via the reception connection unit 22, and is a low noise amplifier that amplifies a reception wave received by the receive antenna 21 and a one-stage source grounded microwave field effect transistor.

The third distributor 24 is a distributor that equally distributes the reception wave, which is amplified by the reception amplifier 23, into two, and is a Wilkinson distributor. One of the reception waves distributed by the third distributor 24 reaches the frequency mixer 26i via the phase shifter 25, and the other reaches the frequency mixer 26q.

The phase shifter 25 delays a phase of the input reception wave by 90 degrees. Thus, outputs of the frequency mixers 26i and 26q do not become 0 at the same time. By providing the phase shifter 25 in this manner, it becomes possible to avoid a null point (point at which an output becomes 0) and judges whether the target object 32 moves to approach or go away. Note that, since such a technique is known, description thereof is omitted.

The frequency mixer 26i is connected to the oscillator 13 via the transmission amplifier 14, the first distributor 15, and the second distributor 16, and further connected to the receive antenna 21 via the reception connection unit 22, the reception amplifier 23, the third distributor 24, and the phase shifter 25. Therefore, an output wave of the frequency mixer 26i is a wave obtained by superposing the transmission wave on the reception wave which is delayed by 90 degrees, and includes a beat component due to the Doppler effect.

The low-pass filter 27i is a frequency filter that passes a low frequency therethrough and does not pass a high frequency therethrough. Accordingly, in the output wave of the frequency mixer 26i, only the beat component having a low frequency passes through the low-pass filter 27i and is output from the output port 28i. The low-pass filter 27i is a known filter circuit such as an RC (Resistor-Capacitor) filter circuit or an LC (Inductor-Capacitor) filter circuit, and configured by general chip parts, so that detailed description thereof is omitted.

Similarly, the frequency mixer 26q is connected to the oscillator 13 via the transmission amplifier 14, the first distributor 15, and the second distributor 16, and further connected to the receive antenna 21 via the reception connection unit 22, the reception amplifier 23, and the third distributor 24. Therefore, an output wave of the frequency mixer 26i is a wave obtained by superposing the transmission wave on the reception wave, and includes a beat component due to the Doppler effect.

The low-pass filter 27q is a frequency filter that passes a low frequency therethrough and does not pass a high frequency therethrough. Accordingly, in the output wave of the frequency mixer 26q, only the beat component having a low frequency passes through the low-pass filter 27q and is output from the output port 28q. Similarly to the low-pass filter 27i, the low-pass filter 27q is a known filter circuit, and configured by general chip parts, so that detailed description thereof is omitted.

Note that, the high frequency device 100 has matched impedance and is only required to perform equal distribution into two, so that the first distributor 15, the second distributor 16, and the second distributor 24 are used and a directional coupler is not required. However, there is no limitation thereto, and a directional coupler may be used appropriately in accordance with a circuit configuration. The directional coupler is able to perform not only impedance matching but also distribution which is not equal distribution.

The transmission connection unit 12 and the reception connection unit 22 are, for example, coaxial lines. The transmission connection unit 12 connects the transmit antenna 11 and the first distributor 15 and transmits a transmission wave. The reception connection unit 22 connects the receive antenna 21 and the reception amplifier 23 and transmits a reception wave.

With the above-described circuit configuration, the high frequency device 100 has a function equivalent to that of the high frequency circuit board 202 illustrated in FIG. 9.

(Circuit Unit)

Figure 2:
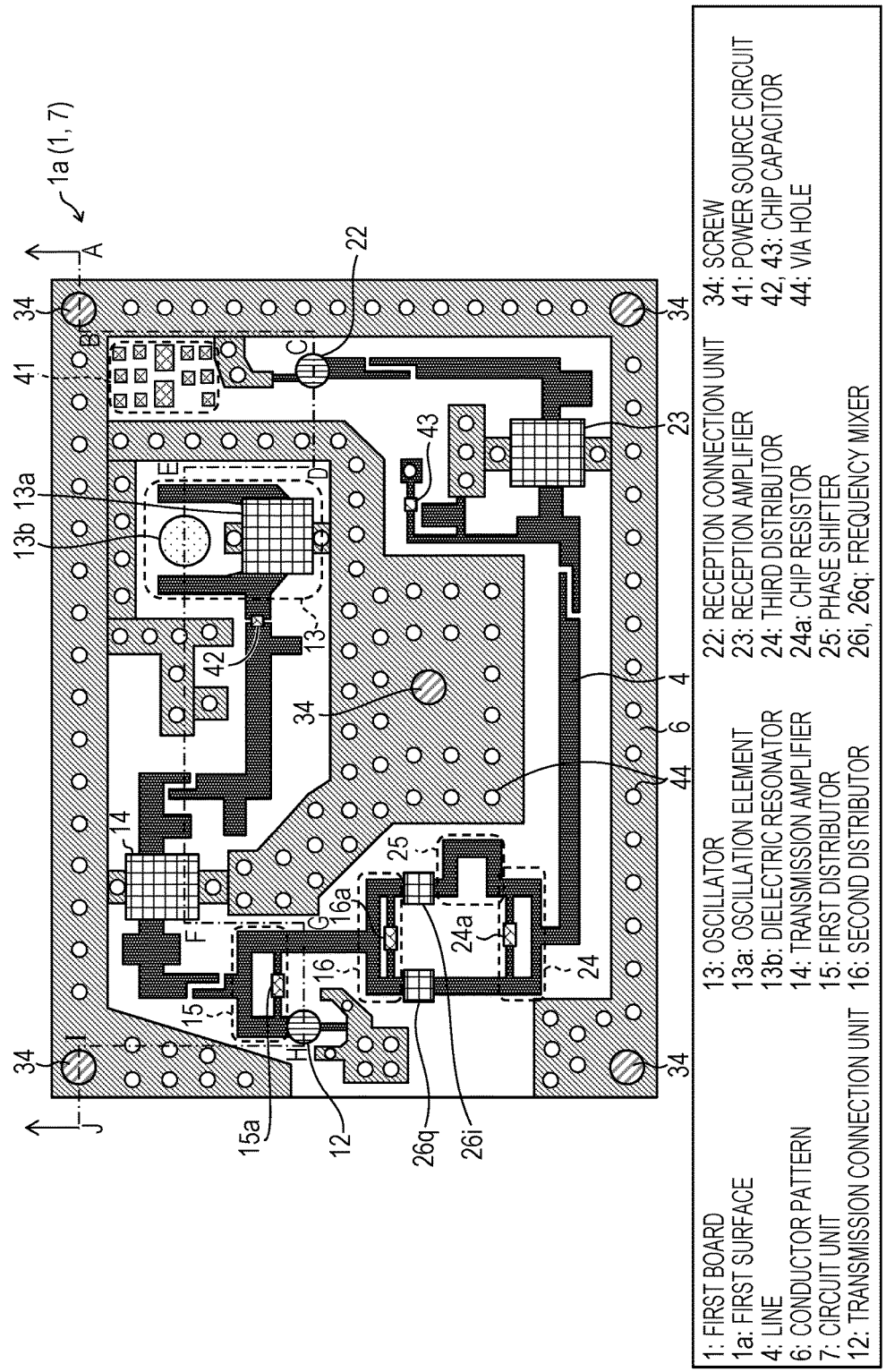
FIG. 2 is a plan view illustrating a schematic configuration of a circuit unit of the high frequency device illustrated in FIG. 1, and illustrates a first surface of a first board.

FIG. 2 is a plan view illustrating a schematic configuration of the circuit unit 7 of the high frequency device 100 illustrated in FIG. 1, and illustrates a first surface 1a of a first single layer board 1 (hereinafter, simply referred to as a first board). Note that, the low-pass filters 27i and 27q and the output ports 28i and 28q which are illustrated in FIG. 1 are low frequency circuits that operate with about 10 kHz or less, so that illustration thereof is omitted in FIG. 2.

The circuit unit 7 is formed on the first surface 1a of the first board 1. On the first board 1, the circuit unit 7 is formed, but the antenna unit 8 is not formed. Thus, a single layer board suitable for forming the circuit unit 7 thereon is able to be selected for the first board 1 by selecting a thickness and a permittivity of a material thereof. Moreover, in order to lower a ground inductance of the circuit unit 7, it is preferable that the first board 1 is thin in accordance with a wavelength (operation wavelength) of an electromagnetic wave, i.e. an operation frequency, of the circuit unit 7 on the first board 1. Specifically, the thickness of the first board 1 is preferably equal to or less than one eighth of the operation wavelength of the circuit unit 7.

The first board 1 is a single layer board on which a microstrip line is formed, and a ground conductor (first ground conductor) is formed of copper foil on an entirety of a surface (referring to FIG. 4, a second surface 1b) opposite to the first surface 1a.

A circuit-side end of the transmission connection unit 12, the oscillator 13 having an oscillation element 13a and a dielectric resonator 13b, the transmission amplifier 14, the first distributor 15 having a chip resistor 15a, the second distributor having a chip resistor 16a, a circuit-side end of the reception connection unit 22, the reception amplifier 23, the third distributor 24 having a chip resistor 24a, the phase shifter 25, the frequency mixers 26i and 26q, a power source circuit 41, chip capacitors 42 and 43, a plurality of via holes 44, lines 4 (transmission lines), and a conductor pattern 6 are provided on the first surface 1a. In addition, five screws 34 pass through the first board 1 at four corners and in a vicinity of a center thereof. As illustrated in FIG. 4, the oscillator 13 is surrounded by a partition conductor 45 which is a ground conductor.

The lines 4 constitute the microstrip line with the ground conductor formed on the second surface 1b. Therefore, each of the lines 4 excellently transmits a high frequency such as a microwave of 24 GHz.

The conductor pattern 6 is electrically and physically connected, via the plurality of via holes 44, to the ground conductor which is formed on the second surface 1b, and is a ground conductor. The conductor pattern 6 is formed in order to ground the respective circuit elements (the oscillation element 13a, the transmission amplifier 14, the reception amplifier 23, the frequency mixers 26i and 26q, the low-pass filters 27i and 27q, and the like) of the circuit unit 7. Moreover, the conductor pattern 6 is formed also in order to ground the partition conductor 45 surrounding the oscillator 13.

The oscillation element 13a is, for example, a microwave bipolar transistor.

The oscillator 13 and the transmission amplifier 14 are connected by the lines 4. Moreover, a gap is provided in the lines 4 between the oscillator 13 and the transmission amplifier 14 so that a direct-current component does not flow. Similarly, the lines 4 each having a gap connect also the transmission amplifier 14 and the first distributor 15, the reception connection unit 22 and the reception amplifier 23, and the reception amplifier 23 and the third distributor.

In such lines 4 each having a gap, a gap capacitor having a sufficient capacitance is formed so that the lines 4 on both sides of the gap are sufficiently connected in a high-frequency manner. Specifically, the lines 4 on the both sides of the gap are formed so that L shapes are alternately inserted. Alternatively, the chip capacitors 42 or 43 each having a sufficient capacitance is provided in the gap so that connection is sufficiently performed in a high-frequency manner. In addition, a stub is provided as appropriate for impedance matching.

The line 4 in which no gap is provided connects the first distributor 15 and the transmission connection unit 12, the first distributor 15 and the second distributor 16, the second distributor 16 and the frequency mixer 26i, the second distributor 16 and the frequency mixer 26q, the third distributor 24 and the frequency mixer 26i, the third distributor 24 and the phase shifter 25, and the phase sifter 25 and the frequency mixer 26q.

Each of the via holes 44 has a via hole conductor formed on an inner wall thereof and is an opening passing through the first board 1. The plurality of via holes are arranged at intervals of 0.8 mm, and connect the conductor pattern 6 to the ground conductor formed on the second surface 1b.

The power source circuit 41 is a low frequency circuit that operates with about 10 kHz or less and is a known technique, so that illustration thereof is simplified and description thereof is omitted.

(Antenna Unit)

FIG. 3 is a plan view illustrating a schematic configuration of the antenna unit 8 of the high frequency device 100 illustrated in FIG. 1, and illustrates a third surface 2a of a second single layer board 2 (hereinafter, simply referred to as a second board).

The antenna unit 8 is formed on the third surface 2a of the second board 2. On the second board 2, the circuit unit 7 is not formed, but the antenna unit 8 is formed. Therefore, a single layer board suitable for forming the antenna unit 8 thereon is able to be selected for the second board 2 by selecting a thickness and a permittivity of a material thereof, thus making it possible to select a single layer board of a type different from that of the first board 1.

The second board 2 is a single layer board on which a microstrip antenna is formed, and a ground conductor (second ground conductor) is formed of copper foil on an entirety of a surface (referring to FIG. 4, a fourth surface 2b) opposite to the third surface 2a.

The line 4, an antenna-side end of the transmission connection unit 12, the transmit antenna 11 having eight transmission patches 11a, an antenna-side end of the reception connection unit 22, and the receive antenna 21 having eight reception patches 21a are provided on the third surface 2a. In addition, five screw receivers 36 are fixed in the third surface 2a at four corners and in a vicinity of a center thereof.

The line 4 constitutes the microstrip line with the ground conductor formed on the fourth surface 2b. Therefore, the line 4 excellently transmits a high frequency such as a microwave of 24 GHz.

The transmit antenna 11 is a microstrip antenna having an array structure constituted by the transmission patches 11a and the ground conductor formed on the fourth surface 2b, but is not limited thereto. Moreover, the receive antenna 21 is a microstrip antenna having an array structure constituted by the reception patches 21a and the ground conductor formed on the fourth surface 2b, but is not limited thereto. In addition, it is preferable that the transmit antenna 11 and the receive antenna 21 have the same configurations so that directivity characteristics thereof are the same. For example, the transmit antenna 11 and the receive antenna 21 may be linear antennas, slot antennas, or the like, each having the same configuration.

The number of the transmission patches 11a is not necessarily eight, and a shape of each of the transmission patches 11a is not limited to a square. Moreover, the number of the reception patches 21a is not necessarily eight, and a shape of each of the reception patches 21a is not limited to a square, either. For example, both of the transmission patches 11a and the reception patches 21a may be nine circular patches whose diameters are mutually slightly different.

(Cross Sectional Structure)

A cross sectional structure of the high frequency device 100 will be hereinafter described.

FIG. 4 is a cross sectional view illustrating a schematic configuration of the high frequency device 100 illustrated in FIG. 1 and illustrates a cross section taken along an arrow A-B-C-D-E-F-J-H-I-J of FIG. 2.

The high frequency device 100 includes the first board on which the circuit unit 7 is formed, the second board 2 on which the antenna unit 8 is formed, a conductor plate 3, a through hole 12c, a conductor pin 12d, a through hole 22c, and a conductor pin 22d that connect the circuit unit 7 and the antenna unit 8, an armor 37 that has a frequency control screw 38 and the partition conductor 45, and five sets of the screw 34, a through hole for a screw 35, and the screw receiver 36.

The conductor plate 3 is a good conductor made of aluminum, copper, or the like, and a plate formed to be flat. The conductor plate 3 functions as a good ground conductor in a wide frequency band from a direct current to an alternating current of a high frequency.

The first board 1 and the second board 2 form a sandwich structure that sandwiches the conductor plate 3. More specifically, the first board 1 and the second board 2 are arranged so that the second surface 1b of the first board 1 and the fourth surface 2b of the second board 2 face each other. The conductor plate 3 is sandwiched between the second surface 1b and the fourth surface 2b. As illustrated in FIG. 2 to FIG. 4, the first board 1, the second board 2, and the conductor plate 3 are tightly fixed by the screws 34 and the screw receivers 36 at five points of the four corners and the vicinity of the center. Note that, the screws 34 and the screw receivers 36 also fix the armor 37.

In this manner, the first board 1 and the second board 2 tightly sandwich the conductor plate 3. Therefore, the ground conductors formed on the second surface 1b of the first board 1 and the fourth surface 2b of the second board 2 are in contact with the conductor plate 3 so as to completely overlap therewith, and are integrated with the conductor plate 3.

Moreover, the circuit unit 7 and the antenna unit 8 are substantially formed on front and rear surfaces (the first surface 1a and the third surface 2a) of one multi-layer board. Since the antenna unit 8 requires an area according to an operation wavelength of the antenna unit 8, it is possible to reduce an area and a size of the high frequency device 100 by forming the circuit unit 7 and other circuits on a surface opposite to the antenna unit 8.

The through hole 12c and the conductor pin 12d form coaxial lines serving as the transmission connection unit 12. The conductor pin 12d connects the first distributor 15 and the transmit antenna 11 via the line 4. Similarly, the through hole 22c and the conductor pin 22d form coaxial lines serving as the reception connection unit 22. The conductor pin 22d connects the reception amplifier 23 and the receive antenna 21 via the line 4.

The armor 37 is cast by die-casting aluminum integrally with the partition conductor 45. The armor 37 is fixed to the first board 1, the second board 2, and the conductor plate 3 by the screws 34 and the screw receivers 36 at four corners and in a vicinity of a center. Moreover, the armor 37 is directly placed on the conductor pattern 6 (refer to FIG. 2) which is formed in an outer edge of the first board 1, and the partition conductor 45 is directly in contact with the conductor pattern 6 formed so as to surround the oscillator 13.

Note that, the partition conductor 45 is required only to form a chamber in which the oscillator 13 oscillates. For example, the partition conductor 45 may be formed separately from the armor 37.

(Ground)

The conductor plate 3 (FIG. 4), the ground conductor formed on the second surface 1b of the first board 1, the ground conductor formed on the fourth surface 2b of the second board 2, the conductor pattern 6 (FIG. 2), the conductor on the inner wall of each of the via holes 44 (FIG. 2, FIG. 4), the screws 34 (FIG. 2, FIG. 4), the screw receivers 36 (FIG. 3, FIG. 4), the armor 37 (FIG. 4), the partition conductor 45 (FIG. 4), and a conductor on an inner wall of each of the through hole 12c and the through hole 22c are grounded during an operation of the high frequency device 100.

The ground plate 3 is grounded.

The ground conductors formed on the second surface 1b and the fourth surface 2b are electrically integrated with the conductor plate 3. Accordingly, the ground conductors formed on the second surface 1b and the fourth surface 2b are grounded. Moreover, the conductor on the inner wall of each of the via holes 44 and the conductor on the inner wall of each of the through hole 12c and the through hole 22c are connected to the conductor plate 3 and grounded.

The conductor pattern 6 is electrically and physically connected to the ground conductor formed on the second surface 1b via the plurality of via holes 44. Accordingly, the conductor pattern 6 is grounded. Furthermore, the via holes 44 are arranged at intervals of 0.8 mm or less, and the first board 1 is sufficiently thin. Thus, according to an electromagnetic wave whose frequency is 24 GHz or less, the conductor pattern 6 and the conductor plate 3 are integrated, and function as an ideal ground conductor.

The armor 37 and the partition conductor 45 are directly in contact with the conductor pattern 6, and therefore grounded.

The screws 34 are directly in contact with the armor 37, so that the screws 34 are grounded. Moreover, the screw receivers 36 are directly in contact with the screws 34, so that the screw receivers 36 are grounded.

As illustrated in FIG. 2, the oscillation element 13a, the transmission amplifier 14, the reception amplifier 23, the frequency mixers 26i and 26q, and the other circuit elements are grounded via the conductor pattern 6.

As above, the conductor pattern 6 and the like are connected to the conductor plate 3 with a low inductance in the high frequency device 100, so that the ground is extremely difficult to be floated. Thus, it is easy to match impedance in an inside of the circuit unit 7, so that a signal (a transmission wave and a reception wave) is efficiently transmitted.

Moreover, the conductor pattern 6 functions as an ideal ground conductor from 0 Hz to 24 GHz. Accordingly, the transmission amplifier 14 and the reception amplifier 23 are able to function with ideal gain characteristics. Similarly, the oscillator 13, the frequency mixers 26i and 26q, and the like are also able to ideally function.

The conductor plate 3 is integrated with the ground conductors formed on the second surface 1b and the fourth surface 2b. Thus, the conductor plate 3 functions as both a ground conductor on a rear side of each of the lines 4 of the circuit unit 7 and a ground conductor on a rear side of the line 4, the transmission patches 11a, and the reception patches 21a of the antenna unit 8. In other words, the circuit unit 7 and the antenna unit 8 share a ground conductor. Since the ground conductor is shared, it is easy to match impedance between the circuit unit 7 and the antenna unit 8, so that a signal (a transmission wave and a reception wave) is efficiently transmitted.

Furthermore, since the ground conductor is shared, it is easy to design impedance, and, for example, it is possible to easily design impedance between the circuit unit 7 and the antenna unit 8 and characteristic impedance between the transmission connection unit 12 and the reception connection unit 22 to be 50Ω to achieve mutual connection. Therefore, it is also easy to design the high frequency device 100.

(Heat Radiation)

Further, the conductor plate 3, the via holes 44, the conductor pattern 6, and the armor 37 function also as a heat radiation path from which heat is radiated. Heat generated in the circuit unit 7 is transferred by the conductor pattern 6 and the via holes 44 and promptly radiated from the conductor plate 3. Alternatively, the heat generated in the circuit unit 7 is transferred by the conductor pattern 6 and promptly radiated from the armor 37. Thus, the circuit unit 7 is difficult to have high temperature and is able to excellently function.

(Connection Unit)

Hereinafter, the through hole 12c and the conductor pin 12d that constitute the transmission connection unit 12 and the through hole 22c and the conductor pin 22d that constitute the reception connection unit 22 will be described in detail.

Figure 5:
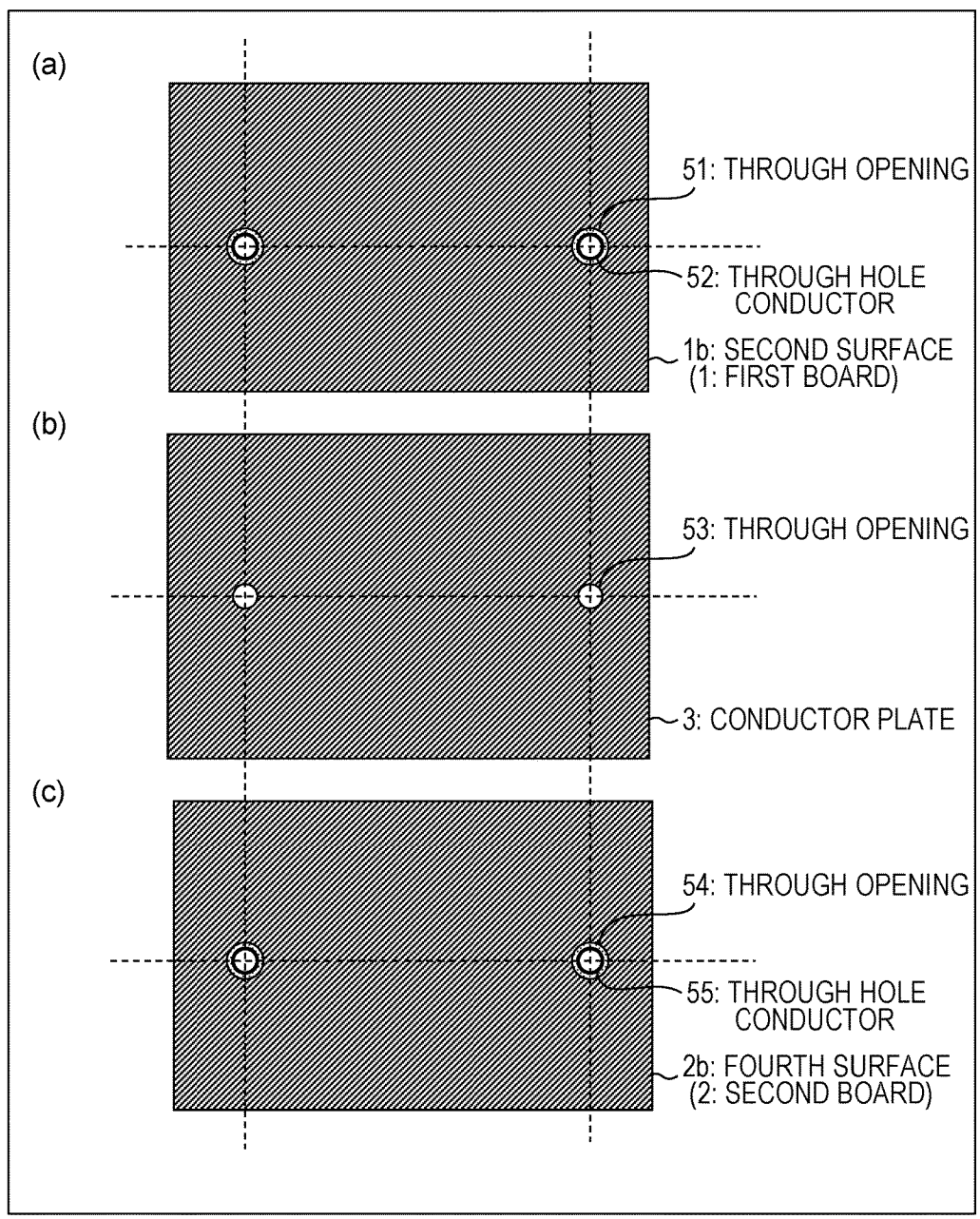
FIG. 5 is a view for explaining through holes illustrated in FIG. 4.

FIG. 5 is a view for explaining the through holes 12c and 22c illustrated in FIG. 4. FIG. 5(a) illustrates the second surface 1b of the first board 1, FIG. 5(b) illustrates the conductor plate 3, and FIG. 5(c) illustrates the fourth surface 2b of the second board 2. Note that, as illustrated in FIG. 4, openings each of which forms the through hole for a screw 35 are formed in the first board 1, the second board 2, and the conductor plate 3, but illustration thereof is omitted in FIG. 5. Moreover, the via holes 44 are formed in the first board 1 as illustrated in FIG. 4, but illustration thereof is omitted in FIG. 5.

Through openings 51, 53, and 54 and through hole conductors 52 and 55 constitute each of the through holes 12c and 22c which are illustrated in FIG. 4. In other words, the through opening 51 and the through hole conductor 52 serve as a part of each of the through holes 12c and 22c, which is formed in the first board 1. The through opening 53 serves as a part of each of the through holes 12c and 22c, which is formed in the conductor plate 3. The through opening 54 and the through hole conductor 55 serve as a part of each of the through holes 12c and 22c, which is formed in the second board 2.

Accordingly, as illustrated in FIG. 5, the through openings 51, 53, and 54 and the through hole conductors 52 and 55 are formed so that center axes thereof are coincident when the first board 1 and the second board 2 sandwich the conductor plate 3. Moreover, since the transmission connection unit 12 and the reception connection unit 22 are coaxial lines, it is preferable that each of the through holes 12c and 22c is a cylinder whose inside diameter is constant. Accordingly, inner diameters of the through hole conductors 52 and 55 and the through opening 53 are equally formed as illustrated in FIG. 5.

With such a configuration, the inner wall of each of the through holes 12c and 22c is the cylinder of a conductor whose inner diameter is constant. Note that, the inner wall is not limited to be the cylinder as long as a cross sectional shape thereof is constant.

In order to match impedance, the transmission connection unit 12 and the reception connection unit 22 are formed so as to achieve equivalent impedance to that of the circuit unit 7 and the antenna unit 8. For example, in a case where the impedance of the circuit unit 7 and the antenna unit 8 is 50Ω, the transmission connection unit 12 and the reception connection unit 22 are formed so that the characteristic impedance becomes 50Ω. Note that, the characteristic impedance of the transmission connection unit 12 is calculated from an inner diameter of the through hole 12c and an outer diameter of the conductor pin 12d and the characteristic impedance of the reception connection unit 22 is calculated from an inner diameter of the through hole 22c and an outer diameter of the conductor pin 22d, which is a known technique.

By matching impedance, the transmission connection unit 12 and the reception connection unit 22 are able to connect the circuit unit 7 and the antenna unit 8 with a low loss. Moreover, it is possible to improve efficiency of the antenna unit 8 and enhance sensitivity of the high frequency device 100.

(Manufacturing Method)

A manufacturing method of the high frequency device 100 will be described below.

First, the first board 1, the second board 2, and the conductor plate 3 are prepared.

Referring to FIG. 2 and FIG. 4, the prepared first board 1 includes the first surface 1a on which the circuit unit 7 is formed and the second surface 1b on the whole surface of which the ground conductor is formed, has the conductor pattern 6 and the via holes 44 formed, and has the through openings 51 each of which passes through between the first surface 1a and the second surface 1b formed. Moreover, each of the through hole conductors 52 is formed so as to cover an inner wall of each of the through openings 51.

Referring to FIG. 3 and FIG. 4, the prepared second board 2 includes the third surface 2a on which the antenna unit 8 is formed and the fourth surface 2b on the whole surface of which the ground conductor is formed, and has the through openings 54 each of which passes through between the third surface 2a and the fourth surface 2b formed. Moreover, each of the through hole conductors 55 is formed so as to cover an inner wall of each of the through openings 54.

The prepared conductor plate 3 has the through openings 53 each of which passes through between front and rear surfaces formed. Note that, the through openings 51, 53, and 54 are formed at positions to be overlapped with each other in plan view when the first board 1, the second board 2, and the conductor plate 3 are overlapped. The first board 1, the second board 2, and the conductor plate 3 have the same shapes in plan view in order to make the positions coincident, but there is no limitation thereto. For example, the conductor plate 3 may be larger than the first board 1 and the second board 2, and the positions may be made coincident by an alignment marker on the conductor plate 3.

Next, the conductor pins 12d and 22d are inserted into the through openings 53, and the conductor plate 3 is sandwiched by the first board 1 and the second board 2 with the positions made coincident. Then, the conductor pins 12d and 22d are connected to the line 4 with solder or the like. Thereby, the transmission connection unit 12 and the reception connection unit 22 are formed, and the circuit unit 7 which is formed on the first board 1 and the antenna unit 8 which is formed on the second board 2 are connected.

Lastly, the armor 37 is overlapped on the first board 1 with a position thereof made coincident, and each of the screws 34 is inserted into each of the through holes for a screw 35 at the four corners and in the vicinity of the center. Then, the screws 34 and the screw receivers 36 at the four corners and in the vicinity of the center are tightened. Thereby, the armor 37, the first board 1, the second board 2, and the conductor plate 3 are fixed to each other.

Note that, the manufacturing method is not limited thereto. For example, the conductor pins 12d and 22d may be inserted into the through holes 12c and 22c after sandwiching the conductor plate 3 between the first board 1 and the second board 2.

(Effect)

An effect specific to the high frequency device 100 will be described below.

As illustrated in FIG. 2 to FIG. 4, the circuit unit 7 is formed on the first board 1 and the antenna unit 8 is formed on the second board 2. Thus, it is possible to select a single layer board which is the most suitable for forming the circuit unit 7 on the first board 1 and select a single layer board which is the most suitable for forming the antenna unit 8 on the second board 2. Accordingly, it is also possible to combine single layer boards of different types, thus making it possible to enhance efficiency of each of the circuit unit 7 and the antenna unit 8.

As illustrated in FIG. 4, the first board 1 and the second board 2 sandwich the conductor plate 3, so that the sandwich structure is formed. Thus, it is possible to integrally handle the first board 1, the second board 2, and the conductor plate 3 as one multi-layer board. In a case of handling them as the one multi-layer board, the first surface 1a and the third surface 2a serve as front and rear surfaces of the substantially one multi-layer board, and the circuit unit 7 and the antenna unit 8 are formed on the front and the rear surfaces of the substantially one multi-layer board.

Accordingly, it is possible to provide the circuit unit 7 on a rear surface (opposite surface) of the antenna unit 8 that requires a large area and, efficiently in terms of an area, arrange the circuit unit 7 and the antenna unit 8 so as to be overlapped with each other in plan view. In addition, another circuit may be further provided on the first surface 1a. For example, a processing circuit that performs processing for a low frequency signal output by the output port 28i or 28q illustrated in FIG. 1 may be provided. It is therefore possible to efficiently reduce the area and the size of the high frequency device 100. Moreover, with the efficient arrangement of the circuit unit 7 and the antenna unit 8, the high frequency device 100 is able to be handled as a small-sized module.

An antenna requires a length which is equal to or more than a half of a wavelength (operation wavelength) of an electromagnetic wave as an operation frequency of the antenna on a board.

Referring to FIG. 9, for example, in a case where the operation frequency is 10 GHz and an effective permittivity of the high frequency circuit board 202 is 4, one antenna needs to have a size of about 7.5 mm or more. Accordingly, when taking arrangement intervals into consideration, sizes of the transmit antenna 203a and the receive antenna 203b which have four antennas arranged in an array become about 5 cm to 7 cm. Furthermore, a length of a long side of the high frequency circuit board 202 including the high frequency circuit unit 211 is about 15 cm, and a length of a long side of the microwave moving body detecting device 201 including the low frequency circuit board 210 is about 20 cm.

On the other hand, referring to FIG. 2 to FIG. 4, the circuit unit 7 is provided on the rear surface of the antenna unit 8 in the high frequency device 100. Therefore, in a case where the operation frequency of the high frequency device 100 is 10 GHz, it is possible to configure the high frequency device 100 so that a length of a long side of the high frequency device 100 is about 10 cm or shorter than 10 cm.

Furthermore, the ground conductors formed on the second surface 1b and the fourth surface 2b and the conductor plate 3 are electrically integrated and become a ground conductor of the first board 1 and the second board 2. Moreover, the conductor plate 3 is a good ground conductor in a direct current and in a wide frequency band from a low frequency to a high frequency. Thus, in the high frequency device 100, the ground is difficult to be floated, and an operation is stable.

On the other hand, a conventional high frequency device that does not have the sandwich structure has a problem that ground is easily floated. A ground conductor formed on a rear surface of a circuit board is generally formed of copper foil, metal coating, or the like to be in a thin film shape. Accordingly, the ground conductor is easy to be divided as islands, or an area of the ground conductor easily becomes small. Then, ground impedance becomes high, so that there is a problem that the ground conductor formed on the rear surface does not function as the ground conductor with respect to a high frequency.

As illustrated in FIG. 4 and FIG. 5, the conductor plate 3 is integrated with the around conductors formed on the second surface 1b and the fourth surface 2b and functions as the good ground conductor of the first board 1 and the second board 2. Thus, the microstrip line formed by the lines 4 and the microstrip antenna formed by the transmission patches 11a and the reception patches 21a substantially share the conductor plate 3 as the ground conductor. In other words, with the conductor plate 3 that is integrated with the ground conductors formed on the second surface 1b and the fourth surface 2b, the lines 4 constitute the microstrip line and the transmission patches 11a and the reception patches 21a constitute the microstrip antenna.

Since the conductor plate 3 is the good ground conductor in a wide frequency band, the ground of the circuit unit 7, the antenna unit 8, the transmission connection unit 12, and the reception connection unit 22 is extremely difficult to be floated, and is shared. Therefore, impedance between the circuit unit 7 and the antenna unit 8 does not fluctuate and becomes stable. Since the impedance is stable, it is easy to match impedance of the circuit unit 7, the antenna unit 8, the transmission connection unit 12, and the reception connection unit 22. By matching the impedance, it is possible to efficiently transmit signal power between the circuit unit 7, the antenna unit 8, the transmission connection unit 12, and the reception connection unit 22. Thus, it is possible to improve power efficiency of the high frequency device 100, reduce power consumption and heat generation of the high frequency device 100, and reduce the size of the high frequency device 100.

Furthermore, the circuit unit 7 and the antenna unit 8 share the conductor plate 3 as the ground conductor and have the stable impedance, so that it is easy to design the impedance.

For example, it is experientially known that, in a microwave frequency band of 3 GHz or more, when a circuit is designed so that impedance becomes about 50Ω, an operation of the circuit is stable from a low frequency to a high frequency and an extra circuit becomes unnecessary, and thus miniaturization is enabled. Accordingly, by designing characteristic impedance of the microstrip line formed by the lines 4, the transmission connection unit 12, and the reception connection unit 22 to be about 50Ω and designing impedance of each circuit in the inside of the circuit unit 7, the transmit antenna 11, and the receive antenna 21 to be about 50Ω, it is possible to stabilize the operation of the high frequency device 100 and reduce the size thereof.

As illustrated in FIG. 2 and FIG. 4, the conductor pattern 6 formed on the first surface 1b is electrically connected to the conductor plate 3 via the via holes 44. The via holes 44 are arranged at intervals of 0.8 mm or less, the operation frequency of the circuit unit 7 is 24 GHz, and an effective permittivity of the first board 1 is about 4. Accordingly, the via holes 44 are arranged at intervals each of which is equal to or less than one eighth of the operation wavelength of the circuit unit 7. Furthermore, the first board 1 is sufficiently thin, and the thickness thereof is equal to or less than one eighth of the operation wavelength. Therefore, the conductor pattern 6 is connected to the conductor plate 3 with extremely low impedance in a wide frequency band from a direct current to the operation frequency of the circuit unit 7. In other words, the conductor pattern 6 functions as an ideal ground conductor in the wide frequency band from a direct current to the operation frequency of the circuit unit 7.

Note that, the arrangement interval between the via holes 44 not limited to 0.8 mm. The arrangement interval between the via holes 44 only needs to be equal to or less than one eighth of the operation wavelength of the circuit unit 7. In a case where the arrangement interval is equal to or less than one eighth, in the wide frequency band from a direct current to the operation frequency of the circuit unit 7, the conductor pattern 6 is connected to the conductor plate 3 with an extremely low inductance and electrically integrated with the conductor plate 3, and has a ground inductance sufficiently reduced. For example, in a case where the operation frequency is 10 GHz, when each of the arrangement interval between the via holes 44 and the thickness of the first board 1 is equal to or less than 2 mm, the conductor pattern 6 functions as an ideal ground conductor.

Since the conductor pattern 6 is the ideal ground conductor, each of the transmission amplifier 14 and the reception amplifier 23 has an extremely low ground inductance and functions with ideal gain characteristics. Moreover, the partition conductor 45 is also directly in contact with the conductor pattern 6, and is therefore an ideal ground conductor. Accordingly, as being surrounded by the partition conductor 45, the oscillator 13 functions with ideal gain characteristics. Furthermore, each of the other circuit elements (the frequency mixers 26i and 26q, the low-pass filters 27i and 27q, and the like) has an extremely low ground inductance and functions with ideal gain characteristics.

Moreover, the conductor pattern 6 is also thermally connected to the conductor plate 3 via the via holes 44. Accordingly, the conductor pattern 6, the via holes 44, and the conductor plate 3 radiate heat generated from the circuit unit 7 and thus also function as an excellent heat radiation path.

The transmission connection unit 12 and the reception connection unit 22 are coaxial lines, and thus connect the circuit unit 7 and the antenna unit 8 in a direct-current manner and in a high-frequency manner, so that it is possible to transmit a transmission wave and a reception wave. Moreover, the characteristic impedance of the transmission connection unit 12 is able to be easily designed from the outer diameter of the conductor pin 12d and the inner diameter of the through hole 12c. The characteristic impedance of the reception connection unit 22 is able to be easily designed from the outer diameters of the conductor pins 12d and 22d and the inner diameters of the through holes 12c and 22c.

Accordingly, it is possible to easily match impedance between the circuit unit 7 and the transmission connection unit 12, between the transmission connection unit 12 and the antenna unit 8, between the antenna unit 8 and the reception connection unit 22, and between the reception connection unit 22 and the circuit unit 7. Therefore, it is possible to reduce impedance mismatching and reduce a loss of signal power between the circuit unit 7 and the antenna unit 8. That is, it is possible to enhance sensitivity of the high frequency device 100.

As illustrated in FIG. 1 to FIG. 4, the high frequency device 100 includes the antenna unit 8 that includes the transmit antenna 11 and the receive antenna 21 and the circuit unit 7 that performs processing for a transmission wave transmitted by the transmit antenna 11 and a reception wave received by the receive antenna 21. Therefore, in addition to transmission of the transmission wave and reception of the reception wave, the high frequency device 100 is able to perform processing by comparing the reception wave with the transmission wave. Specifically, since the frequency mixers 26i and 26q superpose the transmission wave on the reception wave, it is possible to extract only a beat component of the reflection wave 33 obtained by modulating the transmission wave 31.

Accordingly, the high frequency device 100 is suitable to be used for radar, communication, or the like.

Note that, although the high frequency device 100 includes the transmit antenna 11 and the receive antenna 21, the scope of the invention is not limited thereto. For example, a high frequency device that includes a transmit antenna and does not include a receive antenna and a high frequency device that includes a receive antenna and does not include a transmit antenna are also encompassed in the scope of the invention.

Embodiment 2

Embodiment 2 of the invention will be described as follows on the basis of FIG. 6. Note that, for convenience of description, the same reference signs will be assigned to members having the same functions as those of the members described in the above-described embodiment, and description thereof will be omitted.

Figure 6:
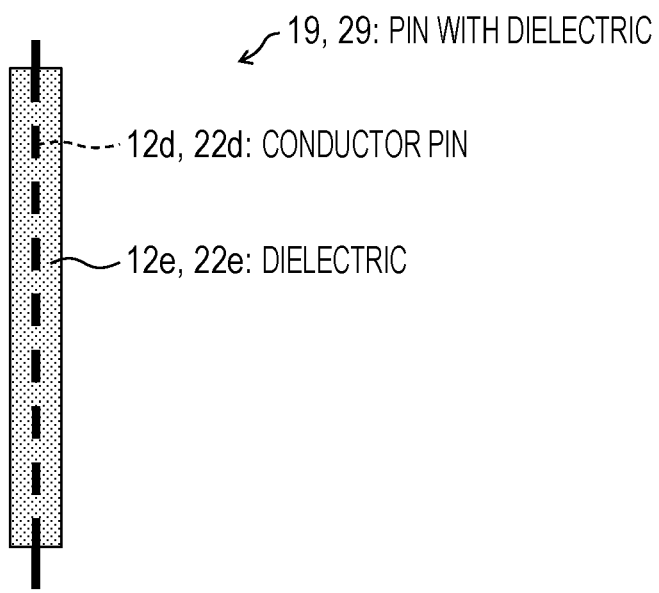
FIG. 6 is a perspective view illustrating a schematic configuration of a pin with a dielectric 19 or 29 used for a high frequency device according to Embodiment 2 of the invention.

FIG. 6 is a perspective view illustrating a schematic configuration of a pin with a dielectric 19 or 29 used for a high frequency device according to Embodiment 2 of the invention.

The pin with a dielectric 19 is a pin in which a dielectric 12e is caused to adhere to a periphery of the conductor pin 12d in a columnar shape. Moreover, the pin with a dielectric 29 is also a pin in which a dielectric 22e is caused to adhere to a periphery of the conductor pin 22d in a columnar shape.

In Embodiment 2, in the high frequency device 100 illustrated in FIG. 4, the pin with a dielectric 19 is used in place of the conductor pin 12d and the pin with a dielectric 29 is used in place of the conductor pin 22d.

In Embodiment 1, there are spaces between the through hole 12c and the conductor pin 12d and between the through hole 22c and the conductor pin 22d. On the other hand, in Embodiment 2, the dielectric 12e is provided between the through hole 12c and the conductor pin 12d and the dielectric 22e is provided between the through hole 22c and the conductor pin 22d.

In Embodiment 2, by the dielectrics 12e and 22e, gaps between the through hole 12c and the conductor pin 12d and between the through hole 22c and the conductor pin 22d are stabilized, the characteristic impedance of the transmission connection unit 12 and the reception connection unit 22 is stabilized, and input impedance and output impedance (hereinafter, input/output impedance) is also stabilized. Thus, when the high frequency device 100 is manufactured, it is possible to stabilize the input/output impedance of the transmission connection unit 12 and the reception connection unit 22 and reduce unevenness.

Furthermore, the pins with a dielectric 19 and 29 assist fixation of the first board 1, the second board 2, and the conductor plate 3 that form the sandwich structure, and facilitate integrating the first board 1, the second board 2, and the conductor plate 3.

Note that, the high frequency device 100 of Embodiment 2, which uses the pins with a dielectric 19 and 29, also has an effect specific to the high frequency device 100 of Embodiment 1.

Similarly to Embodiment 1, it is possible to select, for each of the first board 1 and the second board 2, the most suitable single layer board for each of the circuit unit 7 and the antenna unit 8. Moreover, the circuit unit 7 and the antenna unit 8 are formed on front and rear surfaces of substantially one multi-layer board. Accordingly, it is possible to arrange the circuit unit 7 and the antenna unit 8 efficiently in terms of an area. Furthermore, the ground is difficult to be floated in the high frequency device 100.

The conductor plate 3 functions as the good ground conductor of the first board 1 and the second board 2. Accordingly, the ground of the circuit unit 7, the antenna unit 8, the transmission connection unit 12, and the reception connection unit 22 is extremely difficult to be floated, so that it is easy to match impedance. Further, designing of impedance is easy, and, by designing impedance between each of the circuits in the inside of the circuit unit 7, the transmit antenna 11, and the receive antenna 21 to be about 50Ω, it becomes possible to stabilize the operation of the high frequency device 100 and reduce the size thereof.

The via holes 44 are arranged at intervals each of which is equal to or less than one eighth of the operation wavelength of the circuit unit 7. Furthermore, the thickness of the first board 1 is equal to or less than one eighth of the operation wavelength. Therefore, the conductor pattern 6 functions as an ideal ground conductor in a wide frequency band from a direct current to the operation frequency of the circuit unit 7. Since the conductor pattern 6 is the ideal ground conductor, each of the circuit elements (the oscillation element 13a, the transmission amplifier 14, the reception amplifier 23, the frequency mixers 26i and 26q, the low-pass filters 27i and 27q, and the like) of the circuit unit 7 functions with ideal gain characteristics.

Moreover, the conductor pattern 6, the via holes 44, and the conductor plate 3 function also as an excellent heat radiation path.

Embodiment 3

Embodiment 3 of the invention will be described as follows on the basis of FIG. 7 and FIG. 8. Note that, for convenience of description, the same reference signs will be assigned to members having the same functions as those of the members described in the above-described embodiments, and description thereof will be omitted.

(Circuit Configuration)

Figure 7:
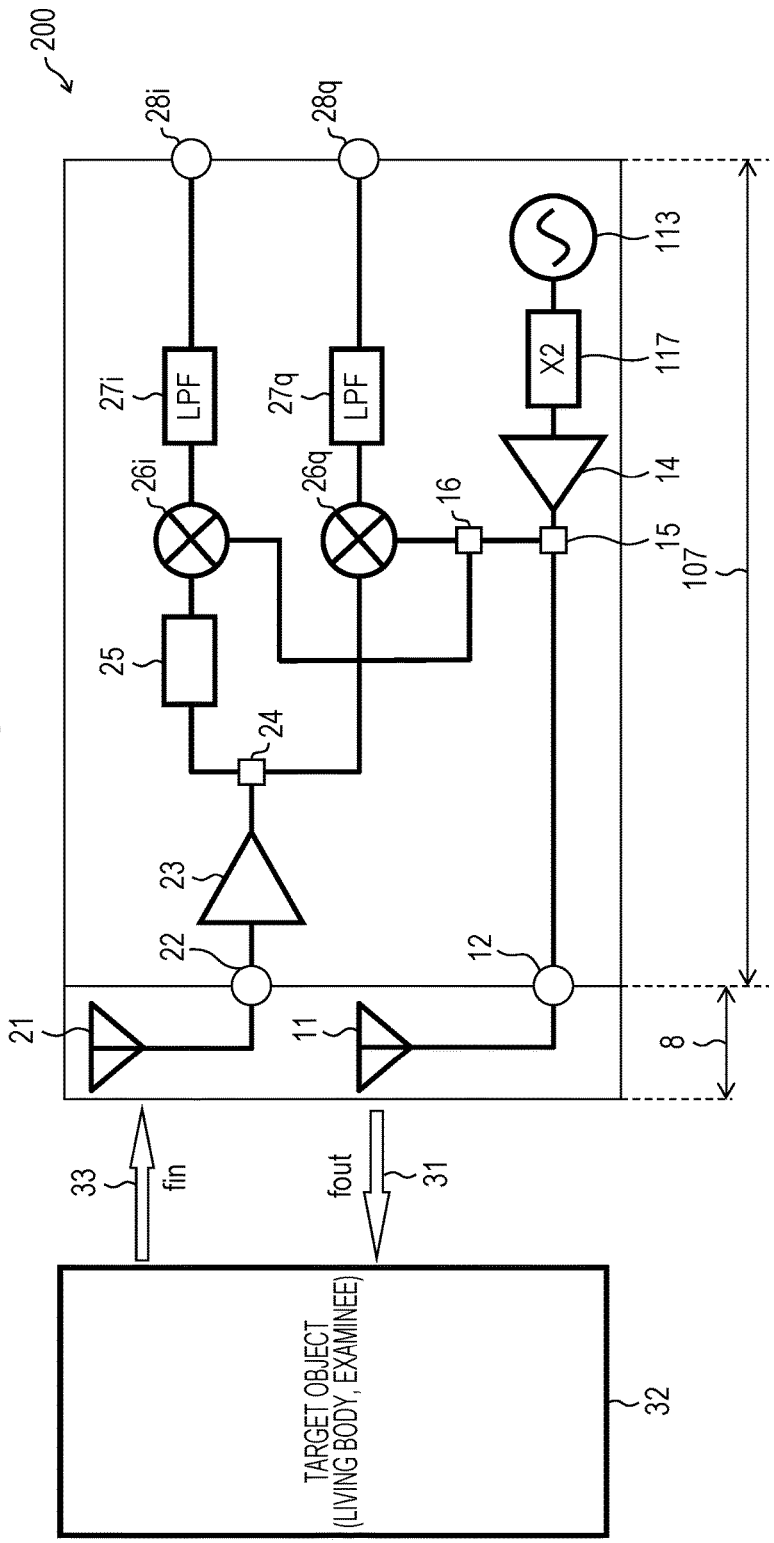
FIG. 7 is a block diagram illustrating a schematic circuit configuration of a high frequency device according to Embodiment 3 of the invention.

FIG. 7 is a block diagram illustrating a schematic circuit configuration of a high frequency device 200 according to Embodiment 3 of the invention. Note that, for simplification of illustration, ground and a power source are omitted in FIG. 7.

The high frequency device 200 includes a circuit unit 107 and the antenna unit 8, and the circuit unit 107 and the antenna unit 8 are connected by the transmission connection unit 12 and the reception connection unit 22.

The circuit unit 107 includes an oscillator 113, the transmission amplifier 14, the first distributor 15, the second distributor 16, a multiplier 117, the reception amplifier 23, the third distributor 24, the phase shifter 25, the frequency mixers 26i and 26q, the low-pass filters 27i and 27q, the output ports 28i and 28q, a power source circuit (not illustrated), and the like. The circuit unit 107 is a transmission circuit that performs processing for a signal transmitted from the antenna unit 8, a reception circuit that performs processing for a signal received by the antenna unit 8, and a high frequency circuit that operates with a high frequency.

The antenna unit 8 includes the transmit antenna 11 and the receive antenna 21.

The oscillator 113 oscillates a microwave of 12.05 GHz. Since an oscillation frequency of the oscillator 113 is low compared with that of the oscillator 13 of Embodiment 1, it is possible to achieve reduction in manufacturing costs of the high frequency device 200 of Embodiment 2.

The multiplier 117 is a frequency multiplier, and multiplies a frequency of an input signal by two. The multiplier 117 multiplies the microwave of 12.05 GHz, which is oscillated by the oscillator 113, to be 24.1 GHz and output the resultant. Accordingly, an operation frequency of each of the circuit unit 107 and the antenna unit 8 becomes about 24 GHz. Note that, the multiplier 117 is not limited thereto, and may multiply the frequency of the input signal by three, for example.

Thus, the high frequency device 200 is different from the high frequency device 100 illustrated in FIG. 1 in that the oscillator 113 and the multiplier 117 are included in place of the oscillator 13. Moreover, when being handled integrally, the oscillator 113 and the multiplier 117 are able to be regarded as an oscillator that transmits a microwave of about 24 GHz. Thus, an operation and a function of the high frequency device 200 of Embodiment 3 are equivalent to those of the high frequency device 100 of Embodiment 1.

(Circuit Unit)

Figure 8:
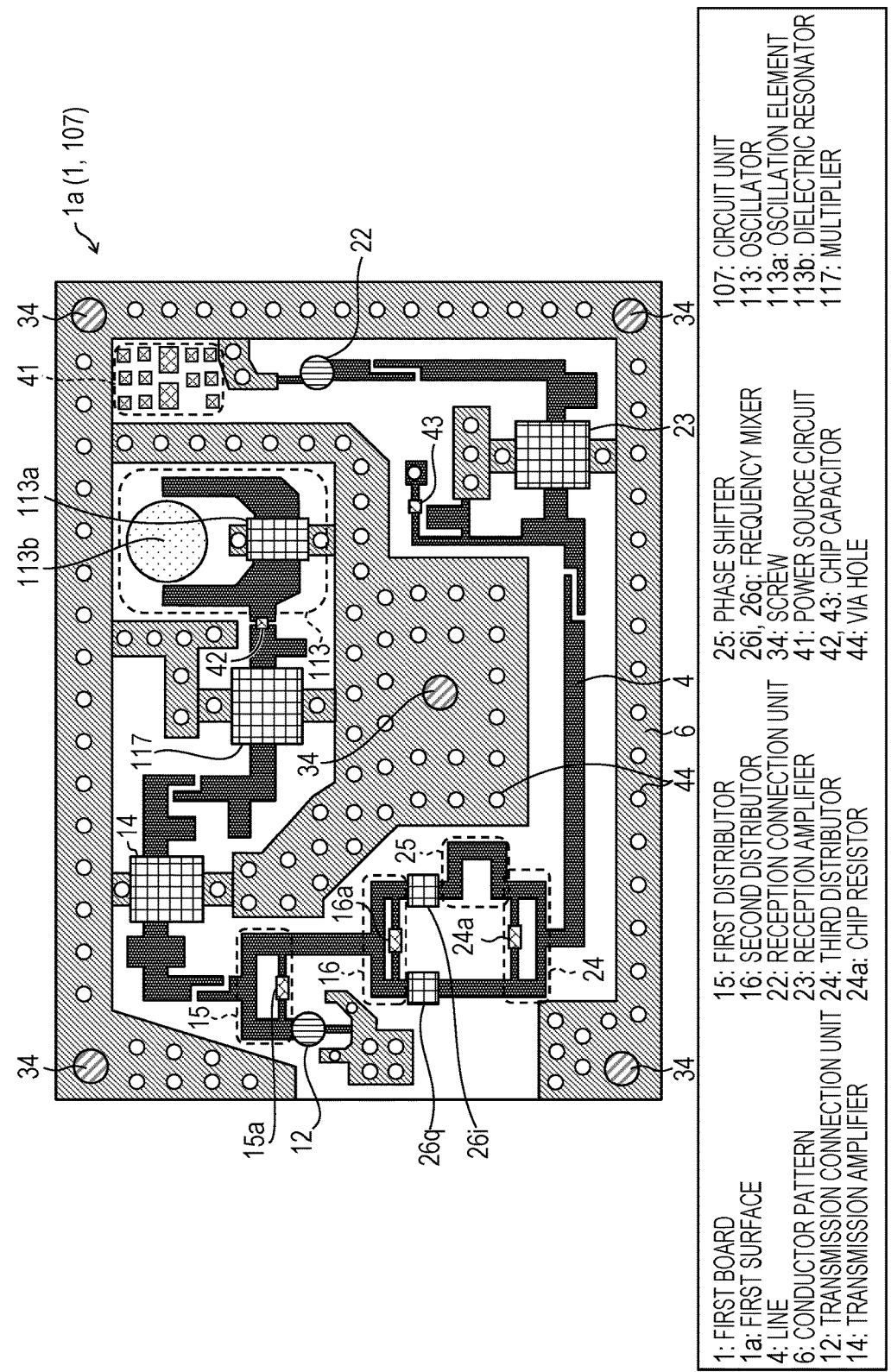
FIG. 8 is a plan view illustrating a schematic configuration of a circuit unit of the high frequency device illustrated in FIG. 7, and illustrates a first surface of a first board.

FIG. 8 is a plan view illustrating a schematic configuration of the circuit unit 107 of the high frequency device 200 illustrated in FIG. 7, and illustrates the first surface 1a of the first board 1. Note that, since the low-pass filters 27i and 27q and the output ports 28i and 28q which are illustrated in FIG. 7 are low frequency circuits that operate with about 10 kHz or less, illustration thereof is omitted in FIG. 8.

The circuit unit 107 is formed on the first surface 1a of the first board 1. On the first board 1, the circuit unit 107 is formed, but the antenna unit 8 is not formed. Therefore, for the first board 1, it is possible to select a board suitable for forming the circuit unit 107 thereon.

The oscillator 113 includes an oscillation element 113a and a dielectric resonator 113b, and is surrounded by the partition conductor 45 (FIG. 4) similarly to the oscillator 13.

The dielectric resonator 113b has a low resonance frequency compared with that of the dielectric resonator 13b of Embodiment 1, and is therefore large.

The oscillation element 113a only needs to oscillate with 12.05 GHz. Thus, a silicon bipolar transistor capable of oscillating in a band of 12 GHz is able to be used as the oscillation element 113a. In a case where the oscillation element 113a is the silicon bipolar transistor, 1/f noise and a no-load Q value of the oscillation element 113a are high, so that the oscillator 113 has excellent phase noise characteristics.

Furthermore, in these years, a phase locked oscillator that uses a phase locked loop (PPL) becomes able to use up to a band of 12 GHz. By using the phase locked oscillator as the oscillator 113, it is possible to enhance stability of the oscillator 113 and reduce a height thereof. Thus, in a case where the oscillator 113 is the phase locked oscillator, the high frequency device 200 has better stability and a size thereof is reduced more.

The multiplier 117 needs to be a nonlinear device and function with both of frequencies of 12.05 GHz and 24.1 GHz. Since the conductor pattern 6 functions as a good ground conductor from 0 Hz to 24 GHz, the multiplier 117 excellently operates.

Note that, the high frequency device 200 has the effect specific to the high frequency device 100 of Embodiment 1.

Similarly to Embodiment 1, it is possible to select, for each of the first board 1 and the second board 2, a single layer board which is the most suitable for each of the circuit unit 7 and the antenna unit 8. Moreover, the circuit unit 7 and the antenna unit 8 are formed on front and rear surfaces of substantially one multi-layer board. Accordingly, it is possible to arrange the circuit unit 7 and the antenna unit 8 efficiently in terms of an area. Furthermore, ground is difficult to be floated in the high frequency device 100.

The conductor plate 3 functions as a good ground conductor of the first board 1 and the second board 2. Accordingly, the ground of the circuit unit 7, the antenna unit 8, the transmission connection unit 12, and the reception connection unit 22 is extremely difficult to be floated, so that it is easy to match impedance. Further, designing of impedance is easy, and, by designing impedance between each of the circuits in the inside of the circuit unit 7, the transmit antenna 11, and the receive antenna 21 to be about 50Ω, it becomes possible to stabilize the operation of the high frequency device 100 and reduce the size thereof.

The via holes 44 are arranged at intervals each of which is equal to or less than one eighth of the operation wavelength of the circuit unit 7. Furthermore, the thickness of the first board 1 is equal to or less than one eighth of the operation wavelength. Therefore, the conductor pattern 6 functions as an ideal ground conductor in a wide frequency band from a direct current to the operation frequency of the circuit unit 7. Since the conductor pattern 6 is the ideal around conductor, each of the circuit elements (the oscillation element 113a, the transmission amplifier 14, the reception amplifier 23, the frequency mixers 26i and 26q, the low-pass filters 27i and 27q, and the like) of the circuit unit 7 functions with ideal gain characteristics.

Moreover, the conductor pattern 6, the via holes 44, and the conductor plate 3 function also as an excellent heat radiation path.

Moreover, the high frequency device 200 is able to perform processing by comparing a reception wave with a transmission wave. Accordingly, the high frequency device 200 is suitable to be used for radar, communication, or the like.

Note that, similarly to Embodiment 2, the pins with a dielectric 19 and 29 illustrated in FIG. 6 may be used in the high frequency device 200 in place of the conductor pins 12d and 22d.

In this case, similarly to Embodiment 2, the characteristic impedance of the transmission connection unit 12 and the reception connection unit 22 is stabilized. Thus, when the high frequency device 100 is manufactured, it is possible to stabilize the input/output impedance of the transmission connection unit 12 and the reception connection unit 22 and reduce unevenness. Furthermore, it is possible to facilitate integrating the first board 1, the second board 2, and the conductor plate 3.

CONCLUSION

A high frequency device (100, 200) according to an aspect 1 of the invention includes: a first single layer board (first board 1) that includes a first surface (1a) on which a high frequency circuit (circuit unit 7, 107) is formed and a second surface (1b) on which a first ground conductor is formed; a second single layer board (second board 2) that includes a third surface (2*a*) on which an antenna (antenna unit 8) is formed and a fourth surface (2*b*) on which a second ground conductor is formed; and a conductor plate (3), in which the conductor plate is sandwiched between the second surface and the fourth surface.

With the aforementioned configuration, the high frequency circuit is formed on the first single layer board, and the antenna is formed on the second single layer board. Accordingly, it is possible to select, for the first single layer board, a board which is the most suitable for forming the high frequency circuit thereon and select, for the second single layer board, a board which is the most suitable for forming the antenna thereon. Therefore, it is also possible to combine single layer boards that are different in a thickness and a permittivity, thus making it possible to enhance efficiency of each of the high frequency circuit and the antenna.

Moreover, with the aforementioned configuration, the first single layer board and the second single layer board sandwich the conductor plate to form a sandwich structure. It is therefore possible to integrally handle the first single layer board, the second single layer board, and the conductor plate as one multi-layer board. In a case where they are handled as one multi-layer board, the first surface and the third surface serve as front and rear surfaces of the substantially one multi-layer board, and the high frequency circuit and the antenna are formed on the front and rear surfaces of the substantially one multi-layer board.

Accordingly, it is possible to provide the high frequency circuit on a rear surface (opposite surface) of the antenna that requires a large area and arrange the high frequency circuit and the antenna efficiently in terms of an area. Thus, it is possible to efficiently reduce an area and a size of the high frequency device.

Moreover, with the aforementioned configuration, first ground conductor, the second ground conductor, and the conductor plate are electrically integrated and become a ground conductor with respect to the first single layer board and the second single layer board. In addition, the conductor plate is a good ground conductor in a direct current and in a wide frequency band from a low frequency to a high frequency. Therefore, in the high frequency device, in the wide frequency band, ground is difficult to be floated and an operation is stabilized.

Since the conductor plate is a good ground conductor, impedances of the high frequency circuit and the antenna do not fluctuate and are stabilized. As being stabilized, impedance is easy to be matched in an inside of the high frequency circuit, in an inside of the antenna, and between the high frequency circuit and the antenna. Moreover, by matching impedance, it is possible to efficiently transmit signal power. It is therefore possible to improve power efficiency of the high frequency device, reduce power consumption and heat generation of the high frequency device, and reduce the size of the high frequency device.

With the aforementioned configuration, the high frequency circuit and the antenna share the conductor plate as the ground conductor and the impedance is stable, so that designing of the impedance is easy.

For example, it is experientially known that, in a microwave frequency band of 3 GHz or more, when impedance is designed to be about 50Ω, an operation is stable from a low frequency to a high frequency and an extra high frequency circuit becomes unnecessary, and thus miniaturization is enabled. Accordingly, by designing the impedance to be about 50Ω, it is possible to stabilize the operation of the high frequency device and reduce the size thereof.

The high frequency device (100, 200) according to an aspect 2 of the invention is the high frequency device according to the aspect 1, in which the high frequency circuit (circuit unit 7, 107) includes a conductor pattern (6) that is connected to the conductor plate by a plurality of via holes (4).

With the aforementioned configuration, it is possible to ground a circuit element in the inside of the high frequency circuit via the via holes and the conductor pattern. Moreover, since the conductor plate, the first ground conductor, the via holes, and the conductor pattern are good heat conductors, a good heat radiation path is formed. This makes it possible to efficiently cool the high frequency device.

The high frequency device (100, 200) according to an aspect 3 of the invention is the high frequency device according to the aspect 2, in which each of arrangement intervals between the plurality of via holes (44) is equal to or less than one eighth of an operation wavelength of the high frequency circuit (circuit unit 7, 107), and a thickness of the first single layer board (first board 1) is equal to or less than the operation wavelength of the high frequency circuit.

With the aforementioned configuration, in a wide frequency band from a direct current to an operation frequency of the high frequency circuit, the conductor pattern is connected to the conductor plate via the via holes and the first ground conductor with an extremely low inductance. In other words, the conductor pattern functions as an ideal ground conductor in the wide frequency band from a direct current to the operation frequency.

Since the conductor pattern is the ideal ground conductor, a circuit element constituting the high frequency circuit functions with ideal gain characteristics. Moreover, thermal connection between the conductor pattern and the conductor plate becomes tight, so that the heat radiation path becomes better. Thus, it is possible to improve the operation of the high frequency device and enhance efficiency of the cooling.

Note that, the operation wavelength means a wavelength of an electromagnetic wave, i.e. the operation wavelength, of the high frequency circuit on the first single layer board.

The high frequency device (100, 200) according to an aspect 4 of the invention is the high frequency device according to any one aspect of the aspects 1 to 3, in which a transmission line (line 4) of the high frequency circuit (circuit unit 7, 107) and the first ground conductor (the ground conductor formed on the second surface 1*b*) form a microstrip line, and the antenna (antenna unit 8) and the second ground conductor (the ground conductor formed on the fourth surface 2*b*) form a microstrip antenna.

With the aforementioned configuration, it is possible to realize a high frequency device that includes the microstrip line and the microstrip antenna.

The high frequency device (100, 200) according to an aspect 5 of the invention is the high frequency device according to any one aspect of the aspects 1 to 4, in which the high frequency circuit (circuit unit 7, 107) and the antenna (antenna unit 8) are connected by a coaxial line (transmission connection unit 12, reception connection unit 22).

With the aforementioned configuration, since the connection is performed by the coaxial line, the high frequency circuit and the antenna are connected excellently in a direct-current manner and in a high-frequency manner and able to transmit a signal.

The high frequency device (100, 200) according to an aspect 6 of the invention is the high frequency device according to claim 6 that is the high frequency device according to the aspect 5, in which a through hole (12c, 22c) and a conductor pin (12d, 22d) in an inside of the through hole form the coaxial line (transmission connection unit 12, reception connection unit 22).

With the aforementioned configuration, it is possible to easily design characteristic impedance of the coaxial line from an outer diameter of the conductor pin and an inner diameter of the through hole. Accordingly, it is possible to easily match impedance between the high frequency circuit and the coaxial line and between the antenna and the coaxial line. Thus, it is possible to reduce impedance mismatching and reduce a loss of signal power between the high frequency circuit and the antenna. That is, it is possible to enhance sensitivity of the high frequency device.

The high frequency device (100, 200) according to an aspect 7 of the invention is the high frequency device according to an aspect 6, in which the through hole (12c, 22c) is provided so that cross sectional shapes are equivalent at parts (through hole conductor 52, 55, through opening 53) that are formed in the first single layer board, the second single layer board, and the conductor plate.

With the aforementioned configuration, the cross sectional shapes of the coaxial ground conductors are constant, so that impedance of the coaxial line does not fluctuate. Accordingly, the high frequency circuit and the antenna are excellently connected.

The high frequency device (100, 200) according to an aspect 8 of the invention is the high frequency device according to an aspect 6 or 7, in which a dielectric (12e, 22e) is provided in a periphery of the conductor pin (12d, 22d).

With the aforementioned configuration, by the dielectric, a gap between the through hole and the conductor pin is stabilized, the characteristic impedance of the coaxial line is stabilized, and input/output impedance is also stabilized. It is therefore possible to reduce unevenness of the input/output impedance of the coaxial line when the high frequency device is manufactured.

Moreover, with the aforementioned configuration, the conductor pin (pin with a dielectric 19, 29) in which the dielectric is provided assists fixation of the first single layer board, the second single layer board, and the conductor plate that form the sandwich structure, and facilitate integrating the first single layer board, the second single layer board, and the conductor plate.

Note that, it is preferable that a cross sectional shape of the dielectric is equivalent to the cross sectional shape of the through hole.

The high frequency device (100, 200) according to an aspect 9 of the invention is the high frequency device according to any one aspect of the aspects 1 to 8, in which the antenna (antenna unit 8) includes a transmit antenna (11) and a receive antenna (21), and the high frequency circuit includes a transmission circuit (the circuit constituted by the oscillator 13 and the transmission amplifier 14) that perform processing for a signal transmitted by the transmit antenna and a reception circuit (the circuit constituted by the reception amplifier 23, the third distributor 24, the phase shifter 25, the frequency mixers 26i and 26q, and the low-pass filters 27i and 27q) that performs processing for a signal received by the receive antenna.

With the aforementioned configuration, in addition to transmission of a transmission wave and reception of a reception wave, the high frequency device is able to perform processing by comparing the reception wave with the transmission wave.

The high frequency device (100, 200) according to an aspect 10 of the invention is the high frequency device according to claim 10 that is the high frequency device according to any one aspect of the aspects 1 to 9 and used for radar or communication.

With the aforementioned configuration, it is possible to realize a high frequency device for radar or communication.

The invention is not limited to each of the embodiments described above and may be modified in various manners within the scope of the claims, and an embodiment achieved by appropriately combining technical means disclosed in different embodiments is also encompassed in the technical scope of the invention. Further, by combining the technical means disclosed in each of the embodiments, a new technical feature may be formed.

INDUSTRIAL APPLICABILITY

The invention is able to be utilized for a communication device, a radar device, and the like each of which uses a high frequency such as a microwave or a millimeter wave. Particularly, the invention is useful for high-speed radio communication, a moving body detecting sensor, a straight sensor, and the like.

REFERENCE SIGNS LIST 1 first board (first single layer board)
2 second board (second single layer board)
3 conductor plate
4 line (transmission line)
6 conductor pattern
7, 107 circuit unit (high frequency circuit)
8 antenna unit (antenna)
11, 203a transmit antenna
11a transmission patch
12 transmission connection unit
12c, 22c through hole
12d, 22d conductor pin
12e, 22e dielectric
13, 113 oscillator
13a, 113a oscillation element
13b, 113b dielectric resonator
14 transmission amplifier
15 first distributor
15a, 16a, 24a chip resistor
16, 24 second distributor
19, 29 pin
21, 203b receive antenna
21a reception patch
22 reception connection unit
23 reception amplifier
24 third distributor
25 phase shifter
26i, 26q frequency mixer
27i, 27q low-pass filter
28i, 28q output port
31 transmission wave
32 target object
22 reflection wave
34 screw
35 through hole for screw
37 armor
38 frequency control screw
41 power source circuit
42, 43 chip capacitor
44 via hole 45 partition conductor
51, 53, 54 through opening (part of through hole)
52, 55 through hole conductor (part of through hole)
100, 200 high frequency device
117 multiplier
201 microwave moving body detecting device
202 high frequency circuit board
210 low frequency circuit board
211 high frequency circuit unit

The invention claimed is:
1. A high frequency device, comprising:
a first single layer board that includes a first surface on which a high frequency circuit and a conductor pattern are formed and a second surface on which a first ground conductor is formed;
a second single layer board that includes a third surface on which an antenna is formed and a fourth surface on which a second ground conductor is formed;
a conductor plate that includes a through opening;
an armor that is configured by a conductor;
through holes that pass through the first single layer board, the second single layer board, and the conductor plate in a straight manner; and
a plurality of screws, wherein
the conductor pattern is
in contact with the armor and
connected to the first ground conductor via a plurality of via holes,
the conductor plate is
sandwiched between the second surface and the fourth surface and
integrated with the first ground conductor and the second ground conductor to configure a ground conductor with respect to both the first single layer board and the second single layer board,
the through opening of the conductor plate, a through hole conductor of the first single layer board, and a through hole conductor of the second single layer board are formed so that center axes thereof are on a straight line, in a case where the first single layer board and the second single layer board sandwich the conductor plate,
the through opening of the conductor plate, the through hole conductor of the first single layer board, and the through hole conductor of the second single layer board are formed so that inner diameters thereof are equivalent,
the through holes include a plurality of first type through holes through which the screws pass, and
by inserting the screws into the first type through holes, the armor, the first single layer board, the second single layer board, and the conductor plate are fixed to each other and grounded.

2. The high frequency device according to claim 1, further comprising
a partition conductor, wherein
the high frequency circuit includes at least one oscillator,
the conductor pattern includes a part that is formed so as to surround the oscillator, and
the partition conductor is in contact with the part of the conductor pattern, which is formed so as to surround the oscillator, and
forms a chamber in which the oscillator oscillates.

3. The high frequency device according to claim 1, wherein
a transmission line of the high frequency circuit and the first ground conductor form a microstrip line, and
the antenna and the second ground conductor form a microstrip antenna.

4. The high frequency device according to claim 1, wherein
the high frequency circuit and the antenna are connected only by a coaxial line.

5. The high frequency device according to claim 1, wherein
the through holes include a second type through hole an inner wall of which is formed of a conductor,
the high frequency circuit and the antenna are connected by a coaxial line, and
the second type through hole and a conductor pin in an inside of the second type through hole form the coaxial line.

6. The high frequency device according to claim 5, wherein
a dielectric is provided in a periphery of the conductor pin.

7. The high frequency device according to claim 5, wherein
the first single layer board includes a through opening,
the second single layer board includes a through opening,
the through hole conductor of the first single layer board covers an inner wall of the through opening of the first single layer board,
the through hole conductor of the second single layer board covers an inner wall of the through opening of the second single layer board, and
the second type through hole includes the through opening of the first single layer board, the inner wall of which is covered by the through hole conductor of the first single layer board, the through opening of the conductor plate, and the through opening of the second single layer board, the inner wall of which is covered by the through hole conductor of the second single layer board.

8. The high frequency device according to claim 5, wherein
the coaxial line has characteristic impedance that is controlled on a basis of a relation of an inner diameter of the second type through hole and an outer diameter of the conductor pin.

* * * * *